United States Patent [19]
West

[11] 3,945,248
[45] Mar. 23, 1976

[54] WIRE BOND INTEGRITY TESTER

[76] Inventor: Harry E. West, 6620 E. Koralee Way, Tucson, Ariz. 85710

[22] Filed: June 9, 1975

[21] Appl. No.: 584,960

[52] U.S. Cl. .................................. 73/88 B; 73/95
[51] Int. Cl.² ....................................... G01N 3/14
[58] Field of Search ........... 73/88 B, 150 A, 95, 103

[56] References Cited
UNITED STATES PATENTS

| | | | |
|---|---|---|---|
| 3,323,357 | 6/1967 | Gloor | 73/103 |
| 3,572,108 | 3/1971 | McShane et al. | 73/141 R |

*Primary Examiner*—Charles A. Ruehl
*Attorney, Agent, or Firm*—Cahill, Sutton & Thomas

[57] ABSTRACT

A vacuum operated testing device measures the bond integrity of wires connected to integrated circuit modules by applying a known and infinitely variable tensile force to the wire under test.

9 Claims, 5 Drawing Figures

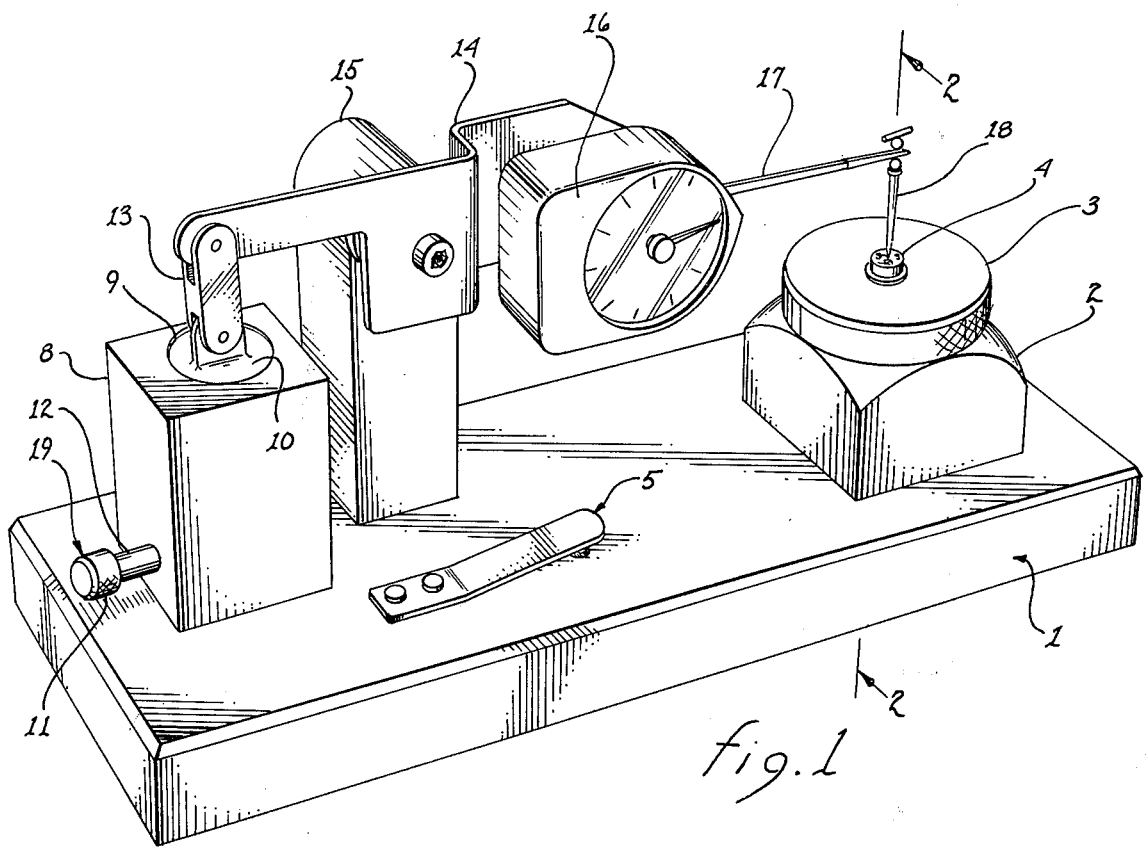
fig.1
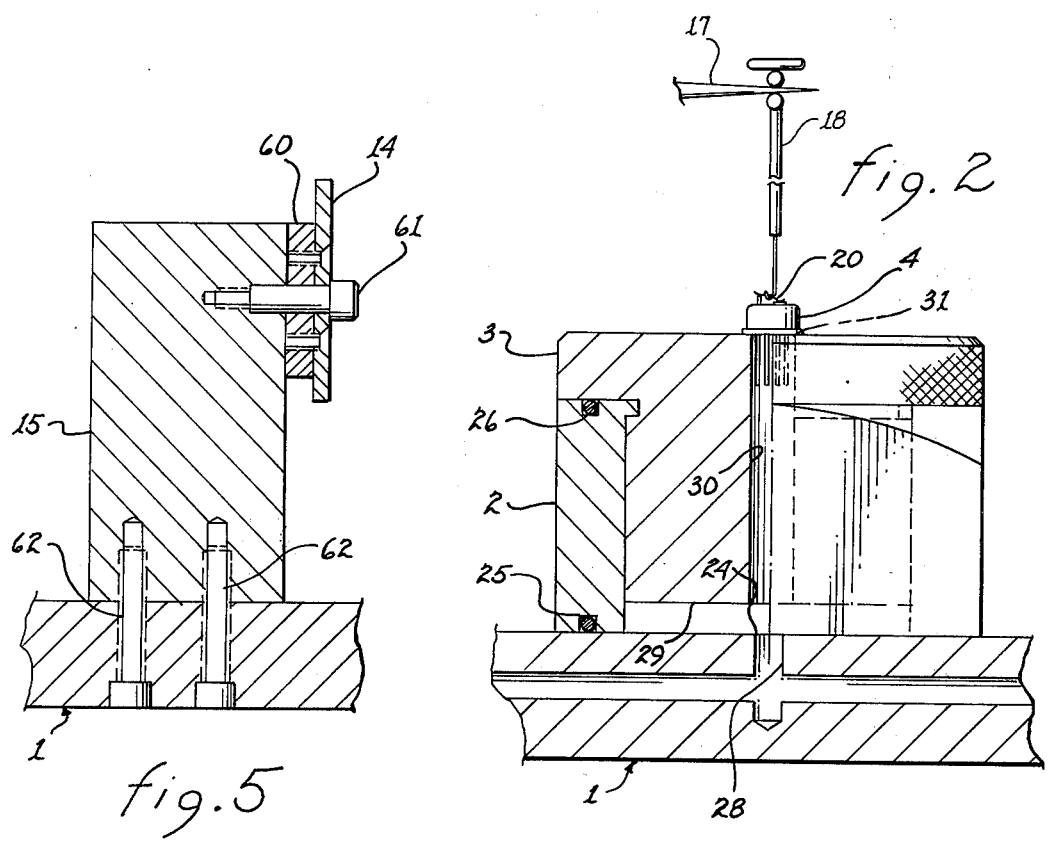
fig.2
fig.5

WIRE BOND INTEGRITY TESTER

The present invention relates to testing devices and, more particularly, to devices for measuring the bond integrity of subminiaturized components.

In present day microelectronic circuit construction techniques, integrated or hybrid circuit chips are attached to electrical conductors, usually pins, by means of fine wires. These fine wires are generally bonded to discrete sections of the chip by well developed bonding techniques. Because of the nature of the bond, testing of the electrical integrity of the bond does not necessarily indicate the presence of a poor or defective bond. To obtain an accurate determination of the integrity of the bond, a pull test on the fine wire must be employed.

The pull test can be performed manually, of course, but because the applied force is measured in terms of grams, destructive testing is essentially meaningless and minimum achievable, non-destructive force levels are quite inaccurate. Consequently, several devices have been developed, which devices apply a force to the fine wire and record the applied force.

One such testing device is described in U.S. Pat. No. 3,572,108, wherein a vacuum is employed to retain the circuit module under test and an electrically driven mechanism is employed to exert a pulling force upon the wire under test. A recording gauge indicates the force applied to the wire at the moment of failure. This tester, although essentially suitable for the purposes intended, is relatively expensive as two different types of power sources (vacuum and electrical) are required; moreover, gear box must be employed to translate the rotary power output of an electric motor to linear movement of the hook engaging the wire under test. Another type of test apparatus is disclosed in U.S. Pat. No. 3,564,911, wherein highly complex mechanical and electromechanical apparatus having multiple adjustments are employed. A further type of tester is disclosed in U.S. Pat. No. 3,581,557; herein, the force applied to a fine wire is generated by means of a pulsed gas discharge.

Other United States patents generally related to testing machines for use in conjunction with subminiature electronic circuitry include U.S. Pat. Nos. 3,127,766; 3,321,961; 3,464,261; 3,634,930; 3,718,035; 3,724,265 and 3,724,264.

It is a primary object of the present invention to provide a simplified wire bond integrity tester.

Another object of the present invention is to provide a totally vacuum operated wire bond integrity tester.

Yet another object of the present invention is to apply a force to a bonded wire at a settable and predeterminable rate.

Still another object of the present invention is to provide a means for instantly relieving the force applied to a specimen under test.

A further object of the present invention is to provide a means for manually controlling the force applied to a specimen under test.

A yet further object of the present invention is to incorporate the same power source for retaining in place the specimen under test and for applying the force to the element of the specimen under test.

An additional object of the present invention is to provide a relatively inexpensive testing device for determining the tensile strength between two bonded subminiature elements.

These and other objects of the present invention will become apparent to those skilled in the art as the description thereof proceeds.

The present invention will be described with greater specificity and clarity with reference to the following drawings, in which:

FIG. 1 is a perspective view of the present invention.

FIG. 2 is a partial cross-sectional view of the platform supporting a work piece.

FIG. 5 is a cross-sectional view taken along lines 5—5, as shown in FIG. 4.

Figure 3:
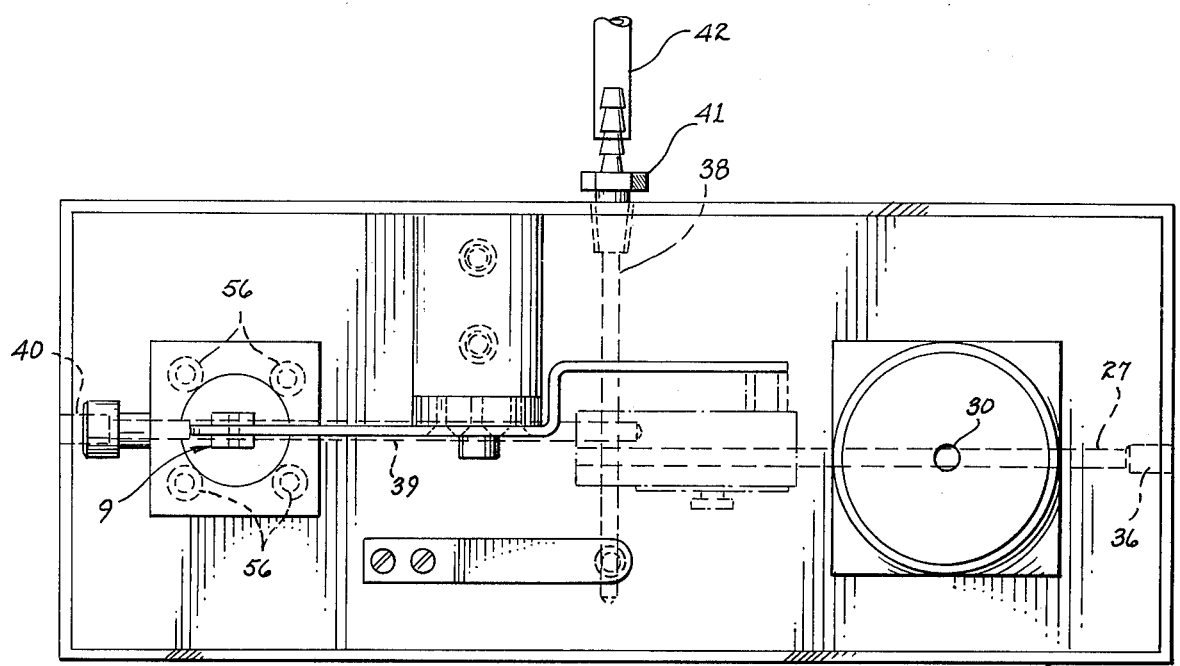
FIG. 3 illustrates the duct work disposed within the base and its relationship to the components mounted upon the base.
Figure 4:
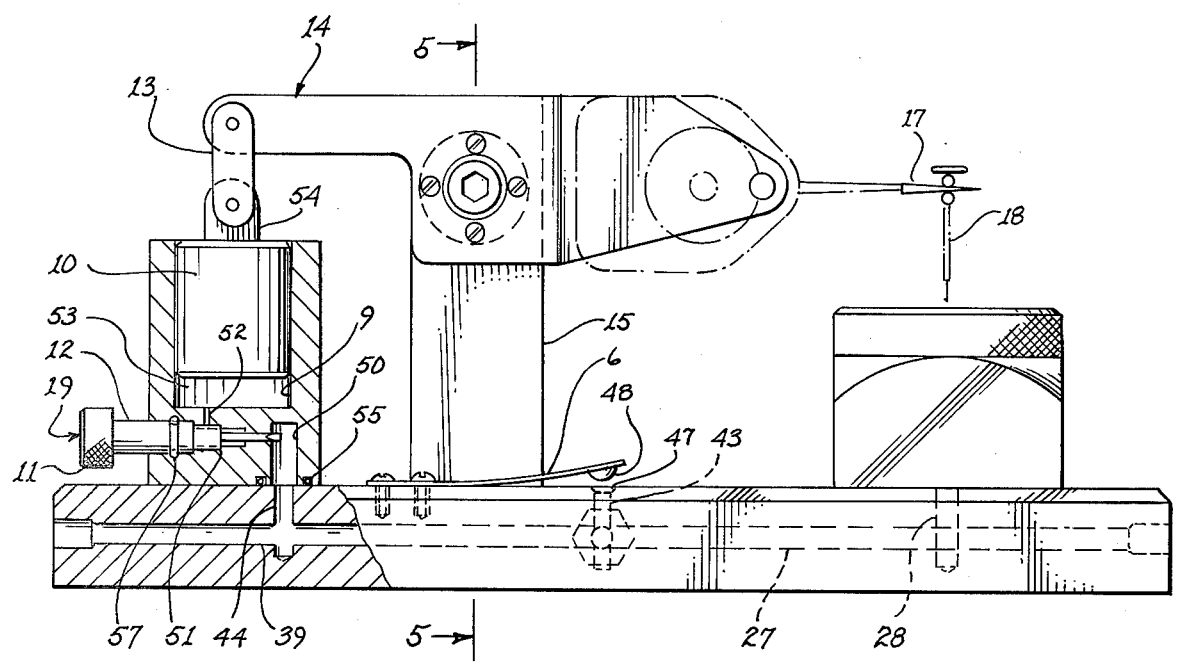
FIG. 4 is a partial cross-sectional view of the present invention.

The overall arrangement of elements and the general operation of the present invention will be described in reference to FIG. 1. A platform 2, mounted upon base 1, supports an adaptor 3, which adaptor positions a microelectronic module or work piece 4. The application of power in the form of a low air pressure source, hereinafter referred to as a vacuum, is controlled by a manually operated valve 5. A pedestal 8 supports a piston 10 within a cylinder 9. Piston 10 is translatable along its longitudinal axis at a rate predetermined by a needle valve 19 within the pedestal. The needle valve is manually regulated through a kurled knob 11 on valve stem 12.

Translatory motion of piston 10 is converted to pivotal movement of arm 14 about a pivot extending from post 15 by means of a double clevis 13 intermediate the piston and one end of the arm. A commercially available recording ram gauge 16 having a pointer and dial, is attached to the other end of arm 14. A gauge such as a Scherr-Tumico dynamometer having a plus and minus 0–15 gram maximum reading dial is particularly suitable for use in conjunction with the present invention. A lever 17 extends from gauge 16 and pivotally supports a needle hook 18. The needle hook may be of many different configurations but a needle hook manufactured and sold by Engineered Technical Products, Inc. is particularly suitable. The hook of needle hook 18 is engaged with a fine wire bonded or otherwise attached to work piece 4.

Platform 2 and its related elements will be described with primary reference to FIG. 2. The platform rests upon but is not mechanically attached to base 1. An O-ring 25 is disposed between the lower surface of the platform and the upper surface of the base to establish an air seal therebetween. Adaptor 3 is removably slidable into engagement with platform 2. An O-ring 26 lodged within a channel in the upper surface of the platform contacts the lower surface of the radially extending section of the adaptor to prevent air leakage intermediate the adaptor and the platform. A generally vertically oriented passageway 30 extends upwardly through the adaptor and is terminated by an aperture 31. Aperture 31 is disposed generally central within the upper surface of the adaptor and supports work piece 4; where the work piece is a microelectronic circuit module having leads or pins extending from the case, the leads or pins are accommodated within passageway 30, and the header of the module rests upon the surface adjacent the opening. By having platform 2 laterally slidable with respect to the bore, the work piece 4 within the adaptor can be positioned such that the fine wire to be tested will be in general alignment with the needle hook. Some latitude in repositioning the needle hook is accommodated by the dual roller or bead-like mechanism engaging the tip of lever 17.

The channeling, distribution and operation of the applied vacuum will be described with joint reference to FIGS. 1, 2, 3 and 4. A source of low pressure or vacuum is introduced through a conduit 42 to fitting 41, which fitting extends from base 1. Fitting 41 interconnects conduit 42 with a passageway 38. Passageway 27 extends from passageway 38 to one edge of base 1 and is sealed by plug 36. A passageway 39 extends from passageway 38 to another edge of base 1 and is sealed by a plug 40. A passageway 28 extends upwardly through base 1 from passageway 27 to an opening 24 circumscribed by platform 2. As may be noted in FIG. 2, the extent to which adaptor 3 penetrates into platform 2 is less than the height of the platform above the base whereby a chamber 29 is formed intermediate the lower end of the adaptor and the upper surface of the base. By incorporating such a chamber, platform 2 can be laterally repositioned within limits to align the fine wire to be tested with the needle hook and yet retain fluid communication intermediate passageways 28 and 30.

A passageway 43 extends upwardly from passageway 38 into operative proximity of valve 5. The valve is defined by a seat 47 at the upper end of passageway 38. Seat 47 is in general alignment with a stopper 48 attached to the underside of a leaf spring 6. By inspection, it will become apparent that passageway 38 is vented to the atmosphere unless the leaf spring is depressed.

A passageway 44 extends upwardly from passageway 39 to the surface of base 1 and provides fluid communication intermediate passageway 39 and a cavity 50 disposed within pedestal 8. An O-ring 55 is disposed between the lower surface pedestal 8 and the base and circumscribes passageway 44 and cavity 50 to prevent air leakage intermediate the pedestal and the base into passageway 44. A needle valve assembly 51 of needle valve 19 is disposed intermediate cavity 50 and a passageway 52 extending downwardly from chamber 53 within cylinder 9. O-ring 57 prevents air leakage adjacent the barrel of the needle valve assembly. The needle valve assembly regulates or meters the flow of air intermediate cavity 50 and chamber 53. Piston 10 is disposed within cylinder 9 and is translatable along its longitudinal axis in response to pressure changes within chamber 53.

From the above discussion, it will be appreciated that passageways 38, 27 and 39 will become at least partially evacuated due to the vacuum or suction introduced through conduit 42 whenever leaf spring 6 is depressed to prevent venting of passageway 38. The resulting vacuum within passageway 27 will be translated through passageway 28 and chamber 29 to passageway 30 and the lower surface of work piece 4. As the ambient air pressure will continue to act upon the upper surface of the work piece, the pressure differential between the upper and lower surfaces of the work pieces will tend to maintain the work piece upon the support. Simultaneously, chamber 53 will, via passageway 44, cavity 50 and passageway 52, be evacuated at a rate commensurate with the setting of needle valve assembly 51. The rate of evacuation of chamber 53 causes a commensurate downward movement of piston 10.

It may be pointed out that a single source of motive force, low pressure supplies the power to retain the work piece in place and to exert a pull test on the fine wire under test.

Referring now jointly to FIGS. 3 and 5, it may be noted that pedestal 8 is rigidly attached to base 1 by means of a plurality of bolts 56. Similarly, post 15 is rigidly attached to base 1 by means of bolts 62. Pivotal movement of arm 14 is accommodated by hub 60 secured to the arm by a plurality of screws. The hub is pivotally supported on the post by means of a shoulder bolt 61. Thereby, arm 14 is free to pivot with respect to the post. Through such rigidity, the force moments translated through arm 14 are precalculatable such that the instrument can be very carefully calibrated.

Although a microscope is not illustrated, the size of the elements being tested generally dictate that one be used to inspect the work piece and element under test before, during and on completion of the test.

In operation, on depressing leaf spring 6 of valve 5, the work piece becomes firmly retained by adaptor 3. Piston 10, being connected to one end of arm 14 by means of ear 54 and double clevis 13, translates downwardly to cause a counterclockwise movement of arm 14. The counterclockwise movement of arm 14 will tend to raise the other end of the arm supporting gauge 16. The gauge itself will, of course, rise but lever 17 extending therefrom is prevented from rising by needle hook 18 engaged to wire 20. The relative movement between lever 17 and gauge 16 is resisted by apparatus internal to the gauge with the moment of resistance exerted being a function of the force applied to wire 20 and displayed on the gauge dial by a pointer. A follower or maximum pointer records the extent of excursion of the dial pointer.

For destructive testing, valve 5 is retained depressed until such time as the bond securing wire 20 fails. At that point, the amount of force applied to the wire can be read directly from the dial. Where the integrity of the wire bond is to be of a certain minimum value, valve 5 is retained depressed until the dial reading corresponds to the amount of force to be applied. When such a force level is obtained, valve 5 is immediately released, which release vents all of the passageways and relieves the force applied to the wire under test.

From the above discussion, it may be apparent that the present invention offers capabilities completely foreign to any of the known prior art. To wit: the base serves as a manifold for channeling the vacuum; a force can be applied at any predetermined rate including that of an impact force; any force applied to a bond under test can be immediately relieved by simply releasing a normally open spring loaded valve.

Other benefits of the present invention include the use of a single motive force, vacuum, which is available at all testing and manufacturing facilities. The orientation and position of the passageways within the base were specifically configured to render them easily and inexpensively borable. The elements forming the present invention are relatively inexpensively manufacturable by artisans of average skill and capability.

The work piece platform was specifically constructed to incorporate vacuum as the retaining force for the adaptor. Thereby, the adaptor can be readily and rapidly replaced. By having a plurality of adaptors, each having a seat commensurate with the configuration of a differently sized work piece, the present invention can be employed to test a plurality of differently sized and configured work pieces.

The present invention can be used efficiently and rapidly to test a large number of work pieces as a single valve is depressed once to secure the work piece in place and to begin to apply the test force. On release of the valve, the applied force is dissipated and the work piece may be removed.

The wire bond tester can be made in sufficiently small sizes for easy transportability. Moreover, a small vacuum pump can operate it so there is no need for an extensive and expensive source of low pressure or vacuum.

While the principles of the invention have now been made clear in an illustrative embodiment, there will be obvious immediately to those skilled in the art many modifications of structure, arrangement, proportions, elements, materials, and components, used in the practice of the invention which are particularly adapted for specific environments and operating requirements without departing from those principles.

I claim:

1. A wire bond integrity tester connected to a source of low pressure for testing the bond which attaches a fine wire to a microelectronic module, said tester comprising in combination:
   a. a base, said base including a manifold in fluid communication with the source of low pressure;
   b. a platform mounted upon said base for supporting the module, said base including a chamber in fluid communication with said module for applying low pressure to the lower surface of the module, whereby, the pressure difference between the low pressure and ambient pressure retains the module in place;
   c. a pedestal mounted upon said base for housing a piston within a cylinder, said piston being axially movable in response to change in air pressure within said cylinder;
   d. air flow regulating means disposed intermediate said cylinder and said manifold for controlling the axial movement of said piston by regulating the flow of air between said cylinder and said manifold;
   e. a pivotable arm mounted above said base for interconnecting said piston with the fine wire, said arm applying a force to the fine wire in proportion to the axial movement of said piston, said arm having gauge means for recording the force applied to the fine wire; and
   f. a normally open vent valve for venting said manifold to ambient air pressure and relieving the force applied to the module and the fine wire; whereby, on closure of said valve a force is applied to retain the module in place and a regulated and recorded test force is applied to the fire wire while maintaining the capability of instantly and simultaneously relieving the module retaining force and the test force applied to the fine wire.

2. The tester as set forth in claim 1, wherein said platform includes a removeable support, said support having an opening disposed therein for receiving the module and includes means disposed intermediate said platform and said support for inhibiting airflow intermediate said platform and said support.

3. The tester set forth in claim 2, wherein said support includes a further passageway extending downwardly through said support from the opening into fluid communication with said chamber, said further passageway applying low air pressure to the module to retain it in place during closure of said vent.

4. The tester as set forth in claim 2, wherein said platform is laterally positionable with respect to said base to accommodate lateral movement of the module and obtain general alignment of the module with said gauge means, said platform further including air seal means disposed intermediate said platform and said base for inhibiting airflow out of said chamber intermediate said platform and said base.

5. The tester as set forth in claim 4, including a post extending upwardly from said base for pivotally supporting said arm.

6. The tester as set forth in claim 5 further including clevis means disposed intermediate one end of said arm and said piston for interconnecting said arm with said piston.

7. The tester as set forth in claim 6, wherein said guage means is attached to another end of said arm, said guage means including a pivotable lever extending therefrom for supporting a needle hook, said needle hook being in engagement with the fine wire under test.

8. The tester as set forth in claim 1, wherein said vent valve comprises a passageway extending from said manifold and terminating at a seat in the upper surface of said base, a downwardly depressible spring leaf having one end attached to said base and the other end generally coincident with said seat, and a stopper extending downwardly from said other end of said leaf spring for mating with said seat; whereby, downward depression of said other end of said leaf spring positions said stopper within said seat to seal said passageway and close the vent for said manifold.

9. The tester as set forth in claim 1, wherein said airflow regulatory means and said vent valve are manually operable.

* * * * *